United States Patent [19]

Miura et al.

[11] Patent Number: 4,909,068
[45] Date of Patent: Mar. 20, 1990

[54] DEVICE FOR DETECTING VISCOSITY OR SPECIFIC GRAVITY OF LIQUID

[75] Inventors: Shinsuke Miura; Susumu Ishizuka, both of Tokyo, Japan

[73] Assignee: Yamaichi Electric Manufacturing Co., Ltd., Tokyo, Japan

[21] Appl. No.: 291,301

[22] Filed: Dec. 28, 1988

[30] Foreign Application Priority Data

Dec. 28, 1987 [JP] Japan ............................ 62-200291[U]

[51] Int. Cl.⁴ .......................... G01N 11/10; G01N 9/10
[52] U.S. Cl. ........................................ 73/32 A; 73/54
[58] Field of Search ................................ 73/32 A, 54

[56] References Cited

U.S. PATENT DOCUMENTS

| | | | |
|---|---|---|---|
| 3,903,732 | 9/1975 | Rork et al. | 73/32 A |
| 3,979,945 | 9/1976 | Kopito et al. | 73/54 |
| 4,217,774 | 8/1980 | Agar | 73/32 A |
| 4,240,285 | 12/1980 | Langdon | 73/32 A |
| 4,811,593 | 3/1989 | Miura et al. | 73/54 |

Primary Examiner—John Chapman
Attorney, Agent, or Firm—Wenderoth, Lind & Ponack

[57] ABSTRACT

A device for detecting the viscosity or specific gravity of liquid has a vibrator, a vibration transmission shaft provided thereon with the vibrator and adapted to transmit the vibration of the vibrator, and a detection terminal connected to one end of the vibration transmission shaft so that the detection terminal immersed in liquid can be vibrated by the vibration of the vibrator. A mass is disposed in a hook-shaped relationship with the vibration transmission shaft at the other end of the vibration transmission shaft. A housing encloses the mass and serves as a grip. A spacer is interposed between the housing and the mass so that the housing is spaced apart from the mass at the peripheral surface thereof, and a vibration absorbing member is mounted on the mass so that the mass is supported by the housing through the vibration absorbing member.

3 Claims, 2 Drawing Sheets

4,909,068

DEVICE FOR DETECTING VISCOSITY OR SPECIFIC GRAVITY OF LIQUID

BACKGROUND OF THE INVENTION

1. Field of the Invention

This invention relates to a device for detecting the viscosity or specific gravity of liquid in which the vibration of a vibrator is transmitted to a detection terminal through a vibration transmission shaft and the viscosity or specific gravity of liquid is detected based on a variation in the vibration of the detection terminal immersed in the liquid.

2. Brief Description of the Prior Art

Conventional detectors measure the viscosity or specific gravity of liquid based on a variation of the vibration of a detection terminal immersed in liquid from the vibration of a vibrator transmitted to the detection terminal through a vibration transmission shaft. The vibration of the vibrator propagates to a housing and if an examiner holds the housing or if the housing is secured to a supporting member, such could cause a disturbance in the vibration, thereby inviting a fluctuation of the frequency or amplitude and thus making it difficult to obtain an accurate measurement.

The present invention has been developed to overcome the above-mentioned problem inherent in the conventional device for detecting the viscosity or specific gravity of liquid.

SUMMARY OF THE INVENTION

It is therefore a general object of the present invention to provide a device for detecting the viscosity or specific gravity of liquid which is capable of measuring the viscosity or specific gravity of liquid correctly.

A specific object of the invention is to provide a device for detecting the viscosity or specific gravity of liquid, in which the interference between the vibration system and the housing, which could be a cause of disturbance adversely affecting measurement, is surely removed so that the viscosity and specific gravity of liquid can be measured accurately.

In order to achieve the above objects, a device for detecting the viscosity or specific gravity of liquid according to the present invention includes a vibrator, a vibration transmission shaft and a detection terminal. The vibrator is mounted on the vibration transmission shaft which is adapted to transmit the vibration of the vibrator to the detection terminal connected to one end of the vibration transmission shaft and immersed in liquid the viscosity or specific gravity of which is to be measured. The device further includes a mass disposed in a hook-shaped relationship with the vibration transmission shaft at the other end of the vibration transmission shaft. The mass is enclosed in a housing serving as a grip. A spacer is interposed between the housing and the mass so that said housing is spaced apart from said mass at the peripheral surface thereof. The mass is supported by the housing at the side of the vibration transmission shaft through a vibration absorbing member.

Preferably, the spacer is disposed at a vibration node in the mass.

According to the present invention, by virtue of the provision of the spacer and the vibration absorbing member, the vibration system including the mass is exactly separated or spaced apart vibrationwise from the housing, the vibration system can be held within the housing in such a fashion as to be exactly spaced apart from the inner peripheral surface thereof, and the mutual interference between the vibration system and the housing, which could cause of disturbance adversely affecting the measurement, can very effectively be removed and as a result, an accurate measurement can be carried out.

The above and other objects and features of the present invention will become apparent from the following description of a preferred embodiment made with reference to the accompanying drawings.

DETAILED DESCRIPTION OF THE PREFERRED EMBODIMENT

Figure 1:
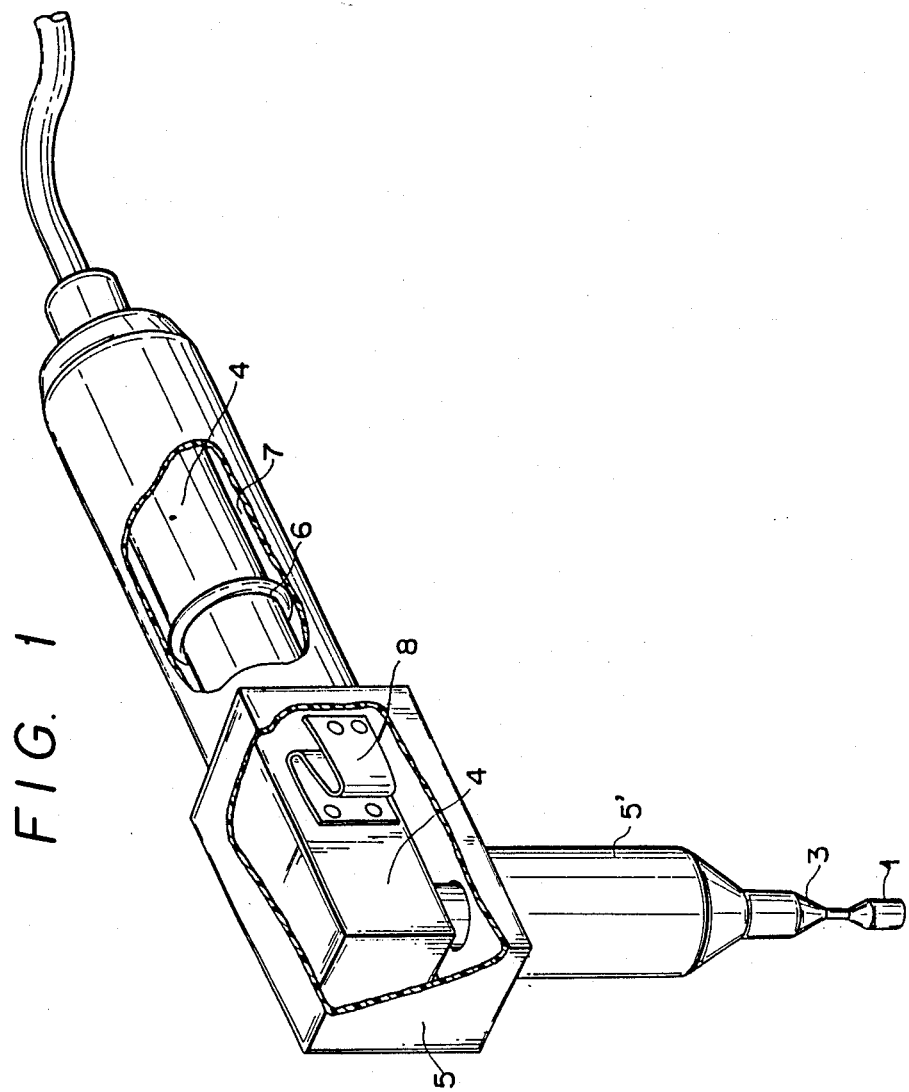
FIG. 1 is a partly cut-away perspective view of a device for detecting the viscosity or specific gravity of liquid according one embodiment of the present invention.
Figure 2:
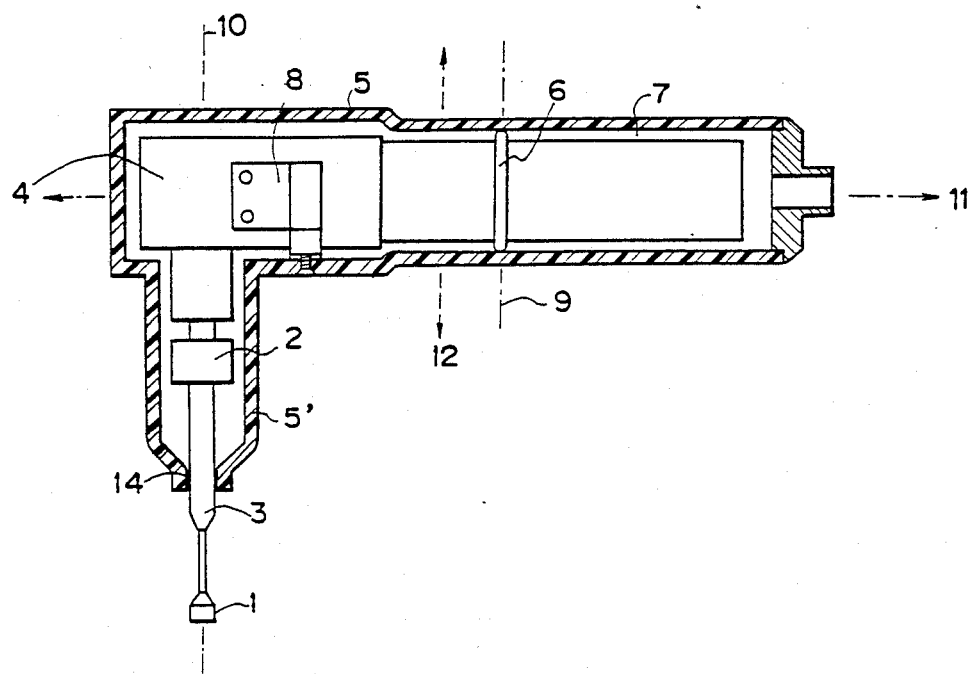
FIG. 2 is a sectional side view of the same.
Figure 3:
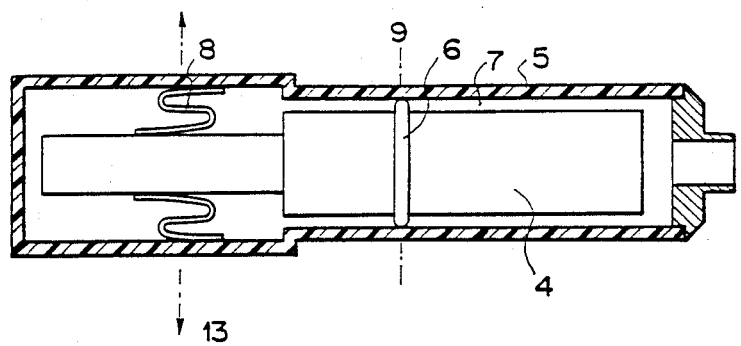
FIG. 3 is a sectional plan view of the same.

One preferred embodiment of the present invention will be described hereunder with reference to FIGS. 1 through 3 of the attached drawings.

The present invention, as previously described, relates to a device for detecting the viscosity or specific gravity of liquid and has a detection terminal 1 which is immersed in a liquid, the specific gravity or viscosity of which is to be measured, and is vibrated. The detection terminal 1 is a column, a rectangular plate or the like. The detection terminal 1 is directly connected to one end of a vibration transmission shaft 3 for transmitting vibration of a vibrator 2. The vibrator 2 is mounted on the vibration transmission shaft 3 so that they have a common vibration axis 10.

The other end of the vibration transmission shaft 3 is provided with a mass 4. The mass is disposed in a hook-shaped relationship with and preferably at right angles with respect to the vibration transmission shaft 3. The periphery of the mass 4 is enclosed in a housing 5 serving as a grip.

The housing 5 is integral with a second housing 5' enclosing the vibration transmission shaft 3 and the vibrator 2.

Interposed between the housing and the mass 4 is a spacer 6 adapted to separate the housing 5 from the mass 4 at a peripheral surface thereof. The spacer 6 is comprising, for example, an elastic ring. The elastic ring is pressfitted to the outer peripheral surface of the mass 4. The elastic ring is further press-fitted to the inner peripheral surface of the housing 5 together with the mass 4.

Due to the foregoing arrangement, the spacer 6 comprising an elastic ring is interposed between the outer peripheral surface of the mass 4 and the inner peripheral surface of the housing 5 in an annular and compressed state, so that the mass 4 is surely held within the housing 5 by the reacting force of the spacer 6 through an annular space 7.

At the same time, the mass 4 held within the housing 5 by the spacer 6 is supported by the housing 5 at the side of the vibration transmission shaft 3 through a vibration absorbing member 8.

The vibration absorbing member 8 is formed of a spring member. Preferably, the spring member is a plate spring as shown in the figures, and the plate spring is U-shaped or undulated. Such a spring member is provided between each pair of opposite surfaces which extend perpendicular to the vibration transmission shaft 3. One end of the spring member is secured to the side surface of the mass 4, whereas the other end is secured to the housing 5.

In this embodiment, the vibrator 2 and the detection terminal 1 are vibration elements vibrating in a circular direction about the vibration transmission axis 10. In this case, the mass 4 is vibrated in the same direction (the rightward and leftward direction designated by 13) as the circular direction of the vibration of the vibrator 2. The center of the vibration is located in the vicinity of the center of gravity of the mass 4. The center of the vibration is referred to as a vibration node 9.

The spacer 6 is disposed at the vibration node 9. In addition, a plate spring forming the vibration transmission member 8 is disposed to each side of the mass 4 in the rightward and leftward direction 13 in such a manner as to oppose each other, and the plate portion of the plate spring is oriented vertically to the vibrating direction of the mass 4. Due to the foregoing arrangement, the mass 4 is rigidly supported by the plate springs with respect to movement in the vertical direction 12 perpendicular to the vibrating direction and to movement in the back and forth direction 11 of the mass 4. Therefore, the mass 4 is restricted to move in various directions by the rigid support and its movement in the rightward and leftward direction 13 is accurately absorbed by the plate springs forming the vibration absorbing member 8.

The mass 4 is coaxial with the housing 5 with the inner peripheral surface of housing 5 spaced apart from the mass 4 by the spacer 6 and the vibration absorbing member 8, and the vibration transmission shaft 3 and the vibrator 2 are disposed along the axis of the housing 5' and are spaced apart from the inner peripheral surface of the housing 5', thus realizing a non-interference state.

Furthermore, the housing 5' provided with the detection terminal 1 projecting from one end thereof defines an annular space 14 formed between the end of the vibration transmission shaft 3 directly connected to the detection terminal 1 and the inner peripheral surface of the housing 5' at its outlet side. Due to the foregoing arrangement, the housing 5' and the vibration transmission shaft 3 do not interfere with each other at the outlet side.

As described above, according to the present invention, a vibration system including a mass is spaced apart from a housing forming a grip by the spacer and the vibration absorbing member, the vibration system is held within the housing in such a fashion as to be accurately spaced apart from the inner peripheral surface thereof, and a mutual interference between the vibration system and the housing, which could cause disturbance adversely effecting the measurement, can very effectively be removed. As a result, the measurement can be carried out accurately.

The present invention has thus been shown and described with reference to a specific embodiment, however, it should be noted that the present invention is in no way limited to the details of the illustrated arrangements but changes and modifications may be made without departing from the scope of the appended claims.

What is claimed is:

1. A device for detecting the viscosity or specific gravity of a liquid, said device comprising:
    a vibrator having a central axis and capable of vibrating about said central axis;
    a vibration transmission shaft having first and second ends and connected coaxially to said vibrator for transmitting vibrations generated by said vibrator;
    a detection terminal connected to said vibration transmission shaft at one end thereof so as to receive vibrations transmitted by said vibration transmission shaft;
    a mass extending longitudinally from the other end of and inclined with respect to said vibration transmission shaft wherein said mass and said vibration transmission shaft constitute hook-shaped structure in which vibrations generated by said vibrator and transmitted to said mass through said vibration transmission shaft tend to vibrate said mass laterally with respect to the longitudinal axis thereof;
    gripping means for allowing the device to be manually gripped in order to immerse said detection terminal in liquid, said gripping means comprising a housing enclosing said mass;
    vibration absorbing means extending between and connected to said housing and said mass for absorbing vibrations in said mass propagating in directions extending laterally of the longitudinal axis of said mass; and
    support means for supporting said mass within said housing, said support means comprising a space interposed between said mass and said housing at a vibration node of said mass at which vibration node vibrations of said vibrator transmitted to said mass by said vibration transmission shaft and propagating in directions extending laterally of the longitudinal axis of said mass are effectively zero in amplitude.

2. A device as claimed in claim 1, wherein said vibration absorbing means comprises a plate spring having a U-shape or an undulated shape and disposed between said mass and said housing laterally of the longitudinal axis of said mass.

3. A device as claimed in claim 1, wherein said vibration absorbing means comprises a pair of plate springs each of which has a U-shape or an undulated shape, said plate springs respectively disposed on opposite sides of said mass laterally of the longitudinal axis thereof.

* * * * *